United States Patent [19]

Brain

[11] Patent Number: 5,305,743

[45] Date of Patent: Apr. 26, 1994

[54] ARTIFICIAL AIRWAY DEVICE

[76] Inventor: Archibald I. J. Brain, St. Andrews, Abney Court Drive, Bourne End, Bucks, United Kingdom

[21] Appl. No.: 3,900

[22] Filed: Feb. 1, 1993

[30] Foreign Application Priority Data

Mar. 5, 1992 [GB] United Kingdom ............... 9204754

[51] Int. Cl.⁵ .................................. A61M 16/00
[52] U.S. Cl. ...................... 128/207.15; 128/200.24; 264/295; 264/501
[58] Field of Search ................ 128/200.24, 207.14, 128/207.15, 204.18; 264/328.1, 295, 501; 156/443, 475; 604/96-103

[56] References Cited

U.S. PATENT DOCUMENTS

| D. 162,333 | 3/1951 | Moore | 446/226 X |
| 1,916,527 | 7/1933 | Pastir | 446/220 |
| 2,804,123 | 8/1957 | Kling | 446/220 X |
| 4,509,514 | 4/1985 | Brain | 128/207.15 |
| 4,995,388 | 2/1991 | Brain | 128/207.15 |

FOREIGN PATENT DOCUMENTS

8101524 6/1981 PCT Int'l Appl. ............... 446/220

Primary Examiner—Edgar S. Burr
Assistant Examiner—Eric P. Raciti
Attorney, Agent, or Firm—Hopgood, Calimafde, Kalil, Blaustein & Judlowe

[57] ABSTRACT

A manufacturing process to produce a laryngeal mask substantially as described in UK Patent GB2205499B consists in a mould which manufactures the inflatable annular ring formation of the device in an inverted form. This allows a more rigid core in the cavity mould or alternatively a dip-moulding process, which in turn permits greater accuracy in control of wall thickness. An alternative form of the mould eliminates the need to assemble a further component, by incorporating the latter into the same single moulding process. And in a further alternative embodiment, the same single moulding process additionally provides an integrally formed inlet for oesophagus drainage, independent of the larynx-venting function of the mask per se.

13 Claims, 4 Drawing Sheets

ARTIFICIAL AIRWAY DEVICE

BACKGROUND OF THE INVENTION

This invention relates to an artificial airway device to facilitate lung ventilation in an unconscious patient, and more specifically to such a device designed for placing in the oropharynx of the patient in order to prevent airway obstruction, to permit either spontaneous or controlled ventilation and to prevent the inhalation into the lungs of extraneous matter such as blood.

To maintain the airway of an unconscious patient, and to achieve the three objectives mentioned above, it is normal practice in general anaesthesia to use an endotracheal tube, which is a flexible tube of rubber or plastics, usually with an inflatable cuff around the distal end. Alternatively, an oro- or naso-pharyngeal airway may be used, which is a flexible tube extending from the mouth or nose into the pharynx but not into the larynx, and which, unlike the endotracheal tube, is used in conjunction with a face mask. While preventing obstruction of the airway by the tongue, the oro- or nasopharyngeal airway cannot conveniently be used for controlled ventilation and does not prevent inhalation of extraneous matter.

The endotracheal tube is introduced through the larynx into the trachea or windpipe, whereupon the cuff is inflated through a small auxiliary tube to seal against the wall of the trachea. Introduction of the endotracheal tube is a skilled operation normally requiring use of a laryngoscope to guide the tube through the larynx, past the vocal cords and into the trachea. There is a risk that the tube or the laryngoscope may cause damage to soft tissues or to the sensitive structures of the larynx. It is not always possible to see the larynx, making intubation difficult or impossible in some patients. There can be a risk of accidental intubation of the oesophagus or of the right or left main bronchus. Placing of the tube in the trachea effectively narrows the interior passage or lumen of the trachea and provides a potential source of damage through infection or pressure while preventing normal upward flow of mucus from the trachea and rendering effective coughing impossible.

My British Patent Specification No. 2111394B describes an artificial airway device comprising a curved or flexible tube and a mask portion carried at one end of the tube. The mask portion has a flexible annular peripheral formation which may be inflatable and which surrounds a hollow interior space or lumen of the mask portion. Said annular peripheral formation of the mask portion is pre-formed with a roughly elliptical shape so as to be capable of conforming to, and of fitting readily within, the actual and potential space behind the larynx, thereby forming a seal around the circumference of the laryngeal inlet without having the device penetrate into the interior of the larynx. The tube opens into the lumen of the mask portion to provide the airway, with the axis of the tube at an acute angle to the general plane of the annular peripheral formation and substantially aligned with the major axis of the roughly elliptical shape of the annular peripheral formation of the mask portion. The device thus constitutes a laryngeal mask.

This device has proved successful in use. Insertion of the device has been found to be easy and convenient in the majority of patients. A laryngoscope is not usually required. The mask does not enter the larynx or trachea, so the risk of damage to these structures is avoided and the tracheal lumen is not narrowed, as is the case upon insertion of an endotracheal tube. The risk of accidental entry into the oesophagus or one of the main bronchi is also avoided. Once in place, the laryngeal mask generally permits the lungs to be ventilated by positive pressure. Alternatively, the patient may be permitted to breathe spontaneously.

An improved laryngeal mask is described in my Patent No. GB 2,205,499B, in which there are provided two flexible cross-bars extending across the aperture in the peripheral annular flexible formation. These bars preferably extend substantially parallel with the major axis of the generally elliptical annular formation. As this patent explains, the parallel bars serve to prevent the epiglottis from blocking the airway passage of the mask.

In the existing laryngeal mask, the peripheral seal formation is an inflatable annulus which, when inflated, is a generally elliptical toroid. Its manufacture presents difficulties, in that the process uses a so-called "floating core" within the outer or female part of the mould. This core is supported by a relatively small pin which ultimately defines the bore of the inflation inlet but which must maintain uniform spacing from the adjacent wall surface of the female mould. It is desired that the wall of the moulded annulus be uniformly thin[1], for example, a selected single thickness in the range 0.4 to 1.0 mm, preferably 0.7 mm. In practice, however, injection of liquid rubber into the mould is under high pressure, and the "floating core" support pin is not capable of resisting small displacements which can cause thickness variations in the wall of the moulded product. In consequence, it has been necessary to maintain a relatively thick wall in the peripheral annular formation so that small changes in wall thickness produced by movement of the core during injection will not result in deformity or rupture of the device when air-inflated in the course of use. The difficulty with a relatively thick wall is that the inflatable annulus is less compliant in adapting itself to the contours of the human pharynx and larynx, thus reducing the efficacy of the desired seal to the laryngeal inlet, and/or unduly limiting the pressure which it is possible to use for inflation of the lungs without loss of seal.

[1] This, for greatest flexiblity in establihsing the intended peripheral seal to the laryngeal inlet; and uniformly thin, to avoid weak areas that might invite herniation.

A further disadvantage of the existing manufacturing process is that it is highly labor-intensive, since the tubular airway portion of the device to which the peripheral annular formation is attached must be connected via a third part, or back plate. This third part is separately moulded and forms an appropriate shape at one end to fit within the peripheral annular formation and at the other end to receive the tubular airway portion of the device. Finally, the back plate and the cut inner periphery of the inflatable ring must be so adhesively secured as to complete the inflatable integrity of the ring as well as the sealing effectiveness of the back plate to the inflatable ring.

BRIEF STATEMENT OF THE INVENTION

The primary object of the present invention is to provide a manufacturing process which will avoid the unwanted movement of the mould core, thus permitting the manufacture of a peripheral annular formation with a significantly thinner wall, with greater precision and at lower cost.

Another object is to meet the above object with a process which lends itself to integrally connected moulding of the inflatable ring and back plate components of the mask in a single operation.

A further object is to meet the above objects with a process which further lends itself to integrally formed provision for an oesophagus-drainage feature in the mask structure.

The invention achieves these objects by providing a mould which is designed to produce a peripheral annular formation substantially identical to that described in my UK Patent No. GB 2,205,499B, but in an inverted form. The moulded part must therefore be inverted before it takes up the desired shape. This inversion is readily achieved provided the part is manufactured from flexible plastic or rubber material or any material which will permit inversion by virtue of its flexibility. The advantage of manufacturing the peripheral annular formation in its inverted form is that the core of the mould required to form this shape does not "float" because, instead of being fixed in place by a relatively small pin, it has a large surface of attachment to remaining parts of the mould. This makes it possible to manufacture the inflatable part with a much thinner and more precisely formed wall since variations in wall thickness are less likely to occur. A further possibility offered by the technique is the use of the core to form the inverted component by a dip-moulding process, in which the core only is dipped into the plastics or rubber material, in liquid form.

Where techniques other than dip-moulding are used, the second-stated object of the invention is realized by eliminating the need for a separate back plate part, in that the moulded back plate is an integral part of the peripheral annular formation.

DETAILED DESCRIPTION OF THE INVENTION

Preferred embodiments of the invention will be described in detail in conjunction with the accompanying drawings. In said drawings.

Referring initially to the embodiment of FIGS. 1 to 4, the invention is shown in application to an inflatable/-deflatable laryngeal mask 10 fitted to the distal end of an airway tube 11, which will be understood to be relatively non-compliant and shaped for manipulated entry of mask 10 into intended position within a patient's pharyngeal cavity, with the proximal end of tube 11 accessible for ventilation via or outside the patient's mouth. The mask 11 comprises a first moulded inflatable/deflatable part (FIGS. 2 and 3) and a second moulded part or back plate 12 (FIG. 2A). In its completed form, the moulded part of FIG. 2 establishes a peripheral inflatable/deflatable element or ring 13 which is toroidal and generally elliptical, wherein the distal end 14 is more pointed and the proximal end 15 is more rounded, in general conformance with similar features of the flat base rim 16 of back plate 12. The more pointed distal end will be understood to be for engagement with and location of the laryngeal mask via the oesophageal inlet, when the elliptical annulus 13 is poised for inflation, via a suitable air-supply line connection 17 at the proximal end of the annulus. Also, consistent with the disclosure of my British patent No. GB 2,205,499B, a flexible membrane 18 closes the lumen of the mask, all except for a passage established by plural adjacent openings which define longitudinal bars 19 between openings, for preventing the epiglottis from blocking the airway passage of the mask.

Figure 4:
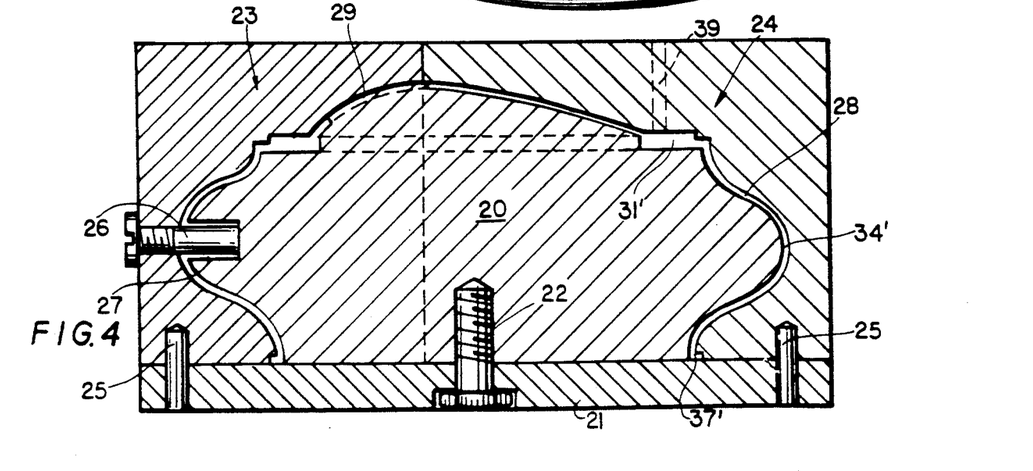
FIG. 4 is a simplified section through a mould for making the component part of FIG. 2.

In accordance with the invention, the mould (FIG. 4) that is used to shape the part (FIG. 2), which will ultimately become the inflatable ring 13, importantly includes a rugged core element 20 which can be accurately and unyieldingly secured to the outer elements of the mould. In FIG. 4, such outer elements are shown to comprise: a base 21 to which core 20 can be secured as by bolt means 22; right and left separable parts 23, 24, which will be understood to be clampable to each other and to plate 21 (by means not shown) but to be accurately located as by dowel pins 25; and a threaded removable pin 26 which enters a local bore 27 in core 20, in order to integrally form the air-supply feature 17.

Figures 2, 3:
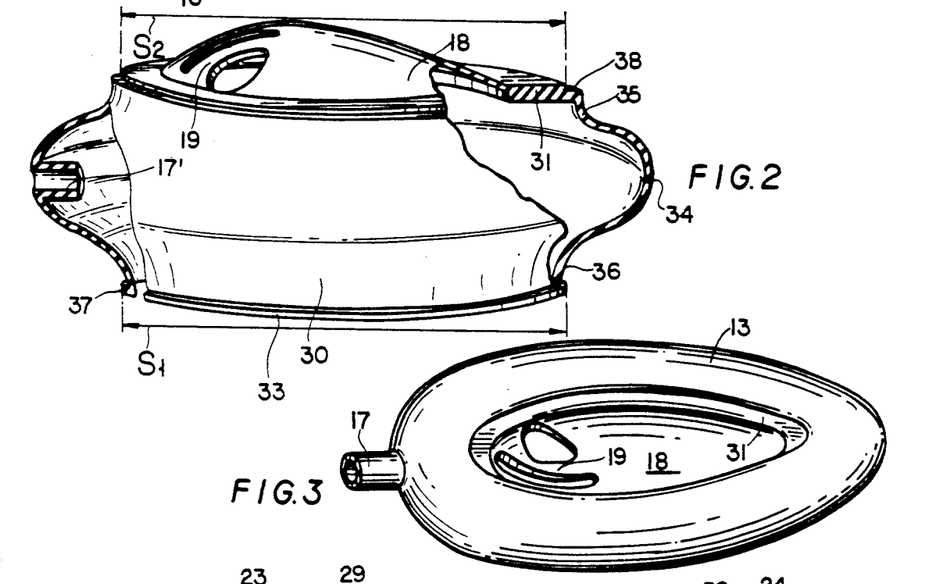
FIG. 2 is a side view in perspective for a first moulded component part of the mask of FIG. 1, portions being broken away and in section, wherein the section plane is the vertical plane of symmetry of the component part.
FIG. 3 is a perspective view of the moulded component part of FIG. 2 after inverting the lower portion thereof, the aspect being from the downstream or laryngeal side of the mask.

A peripherally continuous space 28 between core 20 and the cooperating outer mould parts 20, 21, 23, 24 will be seen to account for the moulded intermediate product of FIG. 2. Briefly, this intermediate product comprises a thin-walled skirt 30, depending from an essentially flat but thicker annulus or flange 31, to the upper inner edge of which a thin-walled shallow dome (flexible membrane 18) effectively closes the lumen within annulus 31, all except for the plural apertures which define longitudinal bars or strips 19 near the proximal end of dome 32. The skirt 30 is characterized by a peripherally continuous lower rim 33 of essentially the same peripheral extent as the outer edge of annulus 31. Between annulus 31 and the lower rim 33, the moulded skirt 30 features a peripherally continuous radially outward convex bulge 34 which becomes concave near its juncture with annulus 31 and near the lower rim 33; in the case of the upper concave portion 35, juncture with annulus 31 is virtually normal to the plane of annulus 31, and in the case of the lower concave portion 36, termination at rim 33 is virtually normal to the geometric lower plane defined by rim 33. Preferably, the moulded longitudinal or major-axis span $S_1$ of the lower end of skirt 30 is substantially equal to or less than the corresponding span $S_2$ between major-axis limits of the upper surface of annulus 31.

As shown, a radially short outward flange formation 37 is a feature of rim 33, resulting from a local mould-cavity feature 37' in the mould of FIG. 4, the same being adjacent to and defined in part by the flat upper surface of the mould base 21. Correspondingly, the radially outer, upper edge of annulus 31 is notched to define a ledge 38 into which flange formation 37 can fit when skirt 30 is flexibly inverted or reversed so as to convert the convex bulge 34 into an outer concave contour which is smoothly contiguous to the concave portions 35 and 36, thereby resulting in virtual completion of the inflatable ring 13 of the mask of FIG. 1. In the process of inversion of skirt 30, what had been an inwardly directed feature 17' of the moulded skirt 30 (FIG. 2) also was reversed to project outwardly and thereby to define the inflation/deflation air-connection feature 17 of inflatable ring 13. The above-stated preferred $S_1/S_2$ relationship will be seen as assuring a natural fit of flange 37 to notch 38, upon inversion of skirt 30.

In the matter of membrane 18 and its apertures with integrally formed bars or strips 19 therebetween, it will be noted that the moulded apertures are shown in FIG. 4 to result from local rounded or ridge-like projecting formations, as at 29 in core 20. Projections 29 will be understood to feature outer-surface convex contouring that conforms precisely to concave contouring of the outer-mould cavity, to and against which projections 29 fit and abut, upon proper mould closure. Thus, at projections 29, mould-core (20) structure offers stabilizing reference to outer-mould structure (e.g., 23) for assurance of uniformly thin development of the moulded skirt 30 which must ultimately be reversed to define inflatable ring 13.

Thus far, mould formations of FIG. 4 have been described only to the extent necessary to form the cavity which will define the intermediate or skirted product of FIG. 2. Various mould designers will have preferences for sprue accommodation, but in FIG. 4, the phantom sprue-passage designation 39 will be understood to suggest an advantage in having the flange-forming cavity 31' serve as an excellent manifold for efficient distribution of the silicon-rubber or the like material that is injected under pressure in the moulding process. Moreover, when the moulded intermediate product of FIG. 2 is cured sufficiently for removal from the mould, the sprue material will readily part company from the thick wall of flange 31, and if such parting leaves a slight upwardly projecting fragment, such fragment will be exposed to view for visual spotting and ready removal, suitably after mould parts 23, 24, 26 have been removed and while the intermediate product of FIG. 2 remains unstripped from core 20. A burr-equipped portable drill is a satisfactory tool for cleaning off any remnant sprue projection, and also for cleaning off any flashing or the like that may be observed at openings of membrane 18.

Having inspected and, if necessary, cleaned up the moulded intermediate product, it is now ready for stripping from the core 20. Since the bottom edge or rim is reinforced by flange formation 37 and is nevertheless flexible and stretchable, the stripping operation involves no more than a local upward peeling of the skirt rim from core 20. Once locally past the bulge 34' of the core, the moulded product is quickly and safely removed and is ready for the simple step of inversion, placing flange 37 into engagement or near-engagement at the peripheral notch 38 of flange 31. Preferably, the engageable surfaces of flanges 37 and 31 will have been first coated with suitable silicone adhesive, in readiness for adhesive completion of ring 13 upon reversal of the skirt 30, as above described. The thus-reversed intermediate product of FIG. 2 will then have the appearance depicted in FIG. 3, as seen from the laryngeal-inlet side.

Figures 1, 2A:
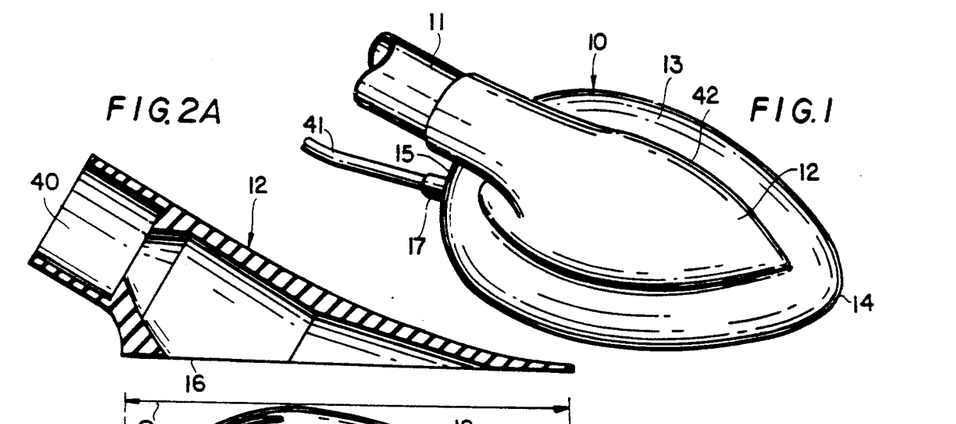
FIG. 1 is a simplified view in perspective, showing a two-piece laryngeal mask of the invention, fitted to the distal end of an airway tube, the aspect being from the upstream or pharyangeal-cavity side of the mask.
FIG. 2A is a sectional view of a second component part of the mask of FIG. 1, the section plane being the same vertical plane of symmetry as in FIG. 2.

The mask of FIG. 1 is then completed by assembling the separately moulded plate component 12 (FIG. 2A) thereto. This component 12 is seen to be of thicker wall structure than skirt 30 and is therefore less compliant, although it may be moulded from the same silicone-rubber material as is the intermediate product of FIG. 2. Its bottom surface 16 is a flat generally elliptical annulus, conforming to the profile of the flat upper surface of flange 31 and extending slightly beyond so as to additionally lap the flat underside of skirt flange 37, after skirt 30 reversal and assembly to notch 38. Again, the bottom surface 16 of plate 12 and the upper exposed surface of flange 31 (with flange 37 in assembled position) will be understood to have been precoated with suitable adhesive, so as to retain the parts of FIGS. 2 and 2A, once they are assembled. The plate 12 of FIG. 2A will then offer its cylindrical counterbore 40 for assembling connection to the airway tube 11, and the inflation formation 17 of the inflatable ring 13 will be ready to accept assembly of the flexible inflation/deflation supply tubing 41 shown in FIG. 1. The mask article of FIG. 1 may then be deemed to be complete, but it is my preference to lay down a bead of silicone adhesive in the peripherally continuous groove 42 established by the adjacency of (a) the outer exposed generally elliptical limiting contour of plate 2 and (b) the now-inverted but previously lower rim of skirt 30. The designation 42 in FIG. 1 will be understood to designate such a bead, which becomes a fillet between adjacent exposed surfaces of plate 12 and ring 13; as described more fully in my copending U.S. patent application Ser. No. 922,132, filed Jul. 30, 1992, such a fillet aids in the desired collapse of ring 13 when evacuated for ease of insertion of the mask of FIG. 1 into and removal of the same from a patient.

Figure 4A:
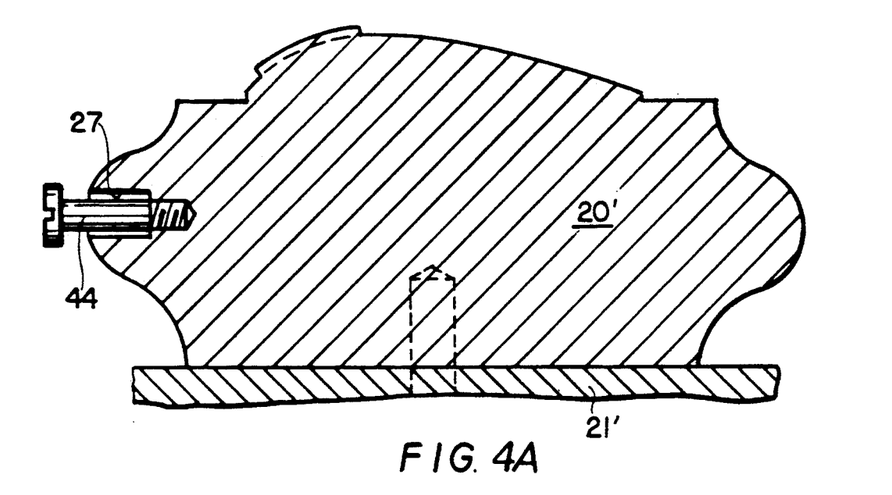
FIG. 4A is a section in the vertical plane of symmetry as in FIG. 4, to show a slightly modified moulding-core element for use in a modified process for making the mask of FIG. 1.
Figure 4B:
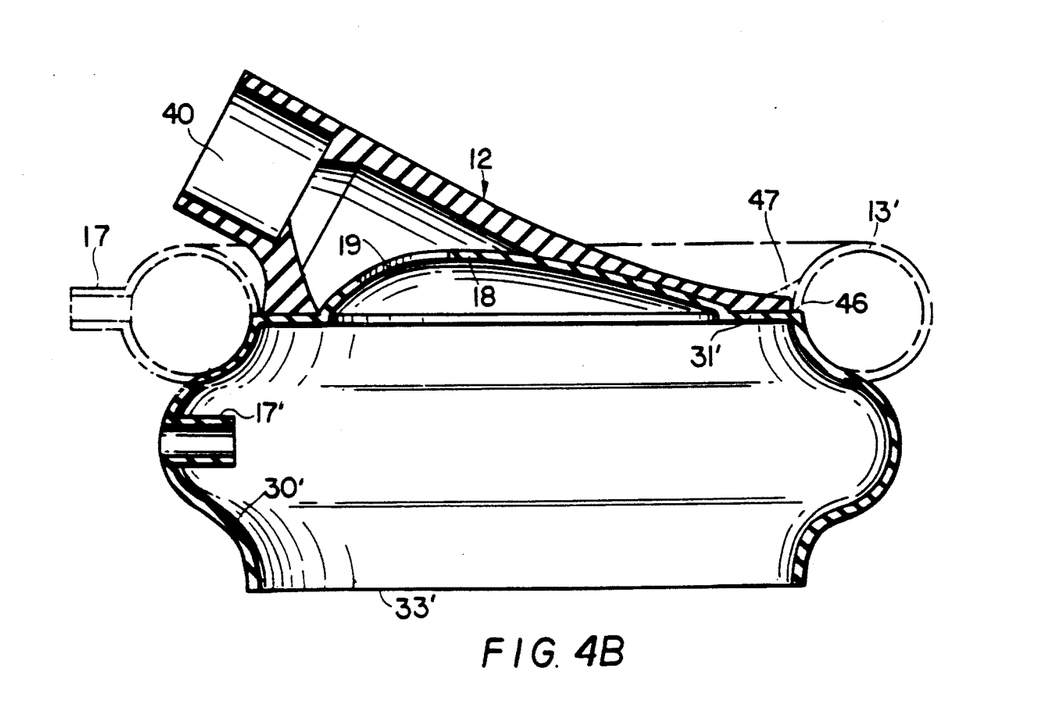
FIG. 4B is vertical section in the plane of symmetry of FIG. 4A, and showing the product of moulding pursuant to FIG. 4A, in assembled relation to the back-plate component of FIG. 2A.

FIGS. 4A and 4B illustrate a simplified technique for manufacture of the described intermediate product, using essentially only the core piece 20 of FIG. 4. In FIG. 4A, the core piece 20' will be recognized as being identical to core piece 20, with the single exception that a threaded plug 44 has been engaged to a tapped hole at the base end of the bore 27 which will ultimately define the inflation/deflation connection 17. The point of FIG. 4A is that the depicted core piece 20' lends itself to so-called dip-moulding, namely, by manipulating core 20' via its base-mounting 21' such that it is inverted and dipped into a pool of liquid moulding material of appropriate viscosity. Dip repetition and total exposure to the liquid moulding material enables wall thickness to build to desired extent, resulting in an intermediate skirted product 45 (FIG. 4B) which closely resembles the product of FIG. 2; the dipped product can be stripped from core 20' after sufficient cure and after unthreading plug 44 from core 20'. The stripped product has the features of FIG. 2 except that there is no flange (37) at the bottom end of skirt 30', and there is no associated notch (38) at the outer periphery of what is now a thin-walled flange 31' against which the conforming flat bottom edge 16 of plate 12 is to be fitted and adhesively retained. The relation of the outer contour of plate 12 to the outer contour of flange 31' is such that a flat outer rim portion 46 remains exposed for adhesively retained reception of the bottom edge 33' of skirt 30', once the skirt 30' has been reversed so as to complete the envelope of an inflatable ring 13'. A filler bead 47 of silicone adhesive is laid down into the exposed groove defined by adjacent surfaces of ring 13' and plate 12, to complete the thus-assembled laryngeal mask, with almost as many of the features as apply to the mask produced from parts and procedures described for FIGS. 1 to 4, but at a mere fraction of the cost for mould parts and pressurizing equipment needed for the procedure of FIGS. 1 to 4.

Figure 5:
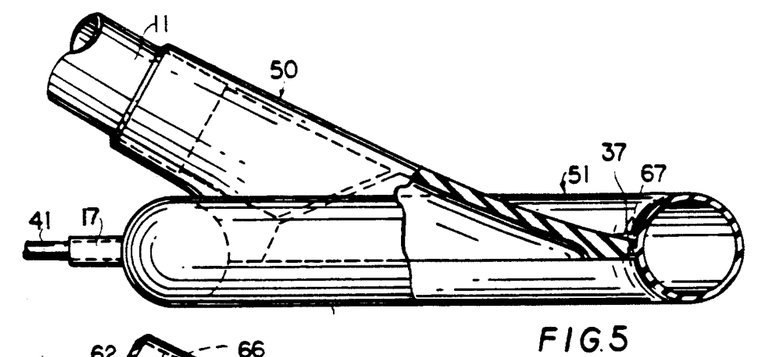
FIG. 5 is a side view in elevation showing a one-piece laryngeal mask of the invention, fitted to the distal end of an airway tube, a portion being broken-away and in section, wherein the section plane is the vertical plane of symmetry of the mask.

In the embodiment of FIG. 5, the back-plate formation 50 is integrally moulded to and as part of the same process as that in which the skirt (FIG. 6) and its inflation/deflation connector 17 are formed, prior to inversion to establish a peripherally continuous inflatable ring 51. The completed laryngeal mask (FIG. 5) is functionally the equivalent of the mask of FIG. 1 and is shown connected in the same way to airway tube 11 and to the supply tubing 41 for inflation/deflation of the inflatable ring 51.

Figure 7:
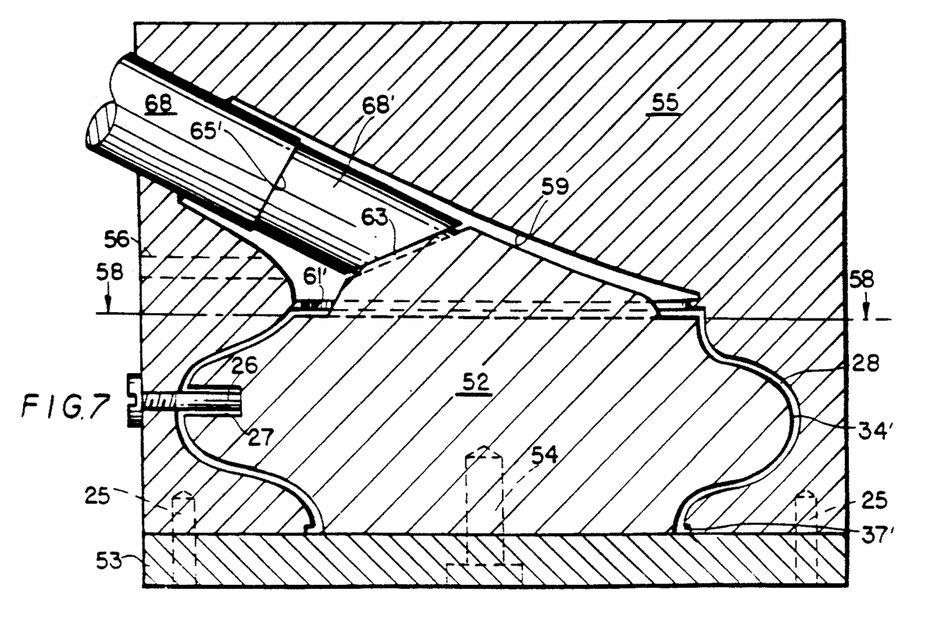
FIG. 7 is a view similar to FIG. 4, specific to the mask of FIG. 5.

More specifically, the mould of FIG. 7, which enables one-step moulding of the entire mask of FIG. 5, is seen to comprise a core 52 having a large area base that is securely referenced to a flat outer-mould base 53 and retained as by bolt means 54. The outer components of the mould are simplified to show establishment of a single cavity in outer-mould structure 55, supplied as by injection of liquid moulding material via one or more sprue passages, suggested at 56.

Figure 6:
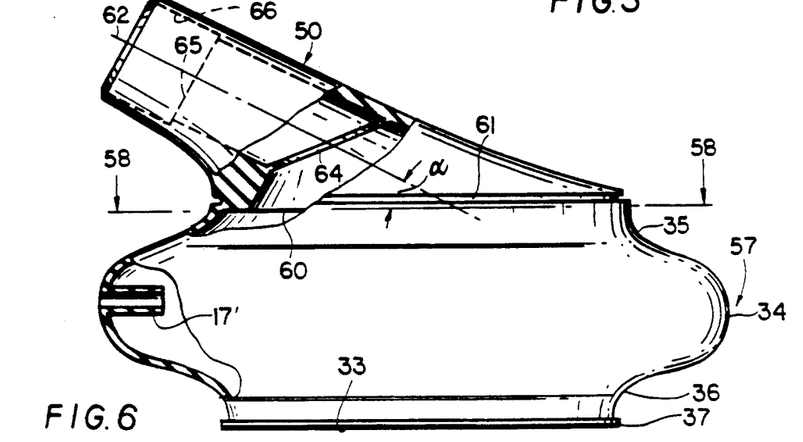
FIG. 6 is a view similar to FIG. 2, specific to the laryngeal mask of FIG. 5.

The back-plate portion 50 of the intermediate moulded product of FIG. 6 is seen to be of greater thickness than the uniformly thin flexible wall of the skirt formation 57 which integrally depends from the geometrical plane of juncture with back-plate 50; in FIGS. 6 and 7 this geometrical plane is identified 58—58. Features of skirt formation 57 may be identical to those of skirt 30 in FIG. 2. Therefore, the same reference numerals have been repeated for skirt 57 in FIG. 6 and for mould-cavity skirt-forming features in FIG. 7.

Above the plane 58—58, the mould-cavity profile 59 is seen to account for essentially the same back-plate external profile at 50 as for the separately moulded part of FIG. 2A. However, at juncture with the flange-like annulus 60 at the base of back-plate formation 50, a peripherally continuous shallow groove 61 is formed by a short inward flange feature 61', sized to provide for located reception of the lower flange 37 of the skirt 57, when inverted. Within the mould cavity and above the plane 58—58, the core 52 rises with a convergent upper body portion which is profiled to establish internal features of the back-plate 50. Specifically, an acute-angle truncation which is at acute inclination to the plane 58—58 and to the axis 62 of airway-tube reception is provided with ridge formations 63 analogous to those at 29 in FIG. 4, to establish the spaced apertures in a membrane 64 for a ventilating flow through the completed mask. In the case of FIG. 7, however, the outer surfaces of formations 63 are flat and in the said plane of truncation, for clean fit to the flat truncated distal end 68' of a mould-cavity defining plug 68 which is retractably guided in a bore of outer-mould structure 55, and which has a shoulder 65' to define a limit stop at 65 in the airway-tube reception bore of plate formation 50.

It will be understood that flexed inversion of skirt 57 of the intermediate moulded product of FIG. 6 will bring lower flange 37 into engagement with groove 61, for adhesively retained completion of the toroidal inflation ring 51. Also, it will be noted that the fitted adjacent surfaces of plate 50 and of the inverted skirt 57, near the lower end of the inverted skirt, will accept the recommended provision of a silicone fillet, suggested at 67 in FIG. 5.

Figures 8, 9:
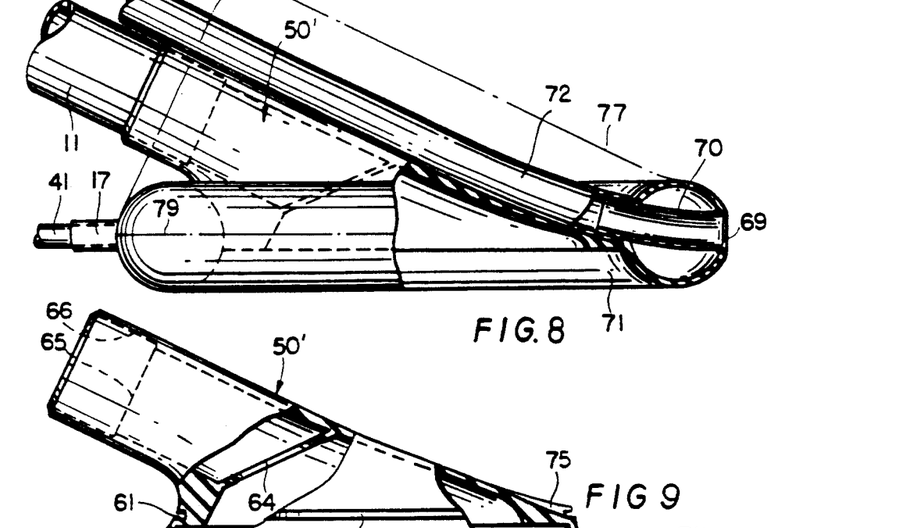
FIG. 8 is a side view in elevation showing another laryngeal mask of the invention, fitted to the distal end of an airway tube, a portion being broken-away and in section, wherein the section plane is the vertical plane of symmetry of the mask.
FIG. 9 is a view similar to FIGS. 2 and 6, but specific to the laryngeal mask of FIG. 8.
Figure 10:
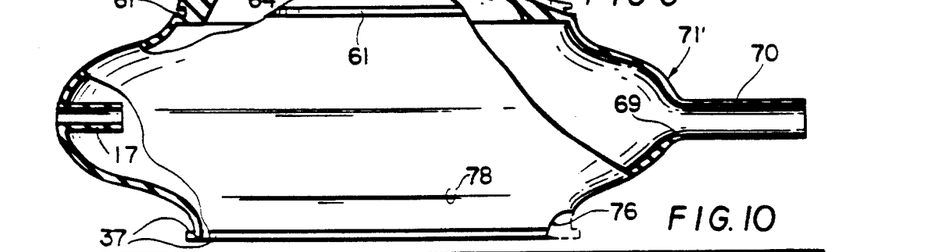
FIG. 10 is a view similar to FIGS. 4 and 7, but specific to the laryngeal mask of FIG. 8.

The embodiment of FIG. 8 and its manufacture are generally as described for the embodiment of FIG. 5, except for the additional provision for oesophagus drainage pursuant to the disclosure of pending U.S. patent application Ser. No. 919,289, filed Jul. 24, 1992. Parts in FIG. 8 and in related FIGS. 9 and 10 which correspond to those of FIGS. 5, 6 and 7 are given the same reference numbers, so that description is thereby simplified. The additional function of oesophagus drainage in FIG. 8 is provided by a re-entrant flexible drainage-tube formation 70, integrally formed with skirt 71 in the single moulding operation which creates the intermediate product of FIG. 9, and which upon skirt reversal, positions the drainage-tube formation 70 upon the upper surface of the back-plate 50' and poised for assembly of flexible tubing 72 thereto, for external evacuation of discharge(s) from the oesophagus.

To accomplish the integrally moulded creation of the drainage-tube formation 70, the outer mould component 55' is shown to have a cylindrical bore 73, for removably connected accommodation of a plug element 74 which is coaxially spaced within bore 73 by reason of threaded mounting near the outer wall surface of outer-mould structure 55'. When in readiness for a moulding operation, the unthreaded end of plug element 74 is either in contact with the most distal bulge forming region 34' of the skirt cavity 28, or, as shown, is fitted into a local bore of core 52, so that core contouring around the open end of the bore can develop a smoothly rounded internal contour 69 (FIG. 9); in FIG. 8, the contour 69 of FIG. 9 is seen to account for the smoothly rounded inlet of the evacuation passage to tube 72.

A shallow groove formation 75 (see FIG. 9) at the distal end of the outer profile of back-plate formation 50' is sized for nested accommodation of the evacuation tube 72, when assembled to tubular formation 70. And a local arcuate "cut-out" 76, defined by a local outer-mould formation 76', enables the skirt 71', upon inversion, to fit over and around tubular fomation 70, thus simplifying the process of securing and sealing the inflatable ring 71 which is produced by inversion of skirt 71'. Having thus completed the assembly of the mask of FIG. 8, it is recommended, as previously, to establish a fillet of silicone adhesive for the full peripheral continuity of lower skirt adjacency (when inverted) to the base profile of back-plate 50', this fillet should extend for full sealing effectiveness around formation 70 at cut-out 76, for inflation/deflation operability of ring 71. At the same time, it is recommended the same adhesive be applied in one or both of the grooves defined by evacuation tube 72 and by the adjacent upper longitudinal profile of back-plate 50', thereby adding a measure of back-plate reinforcement to the adhesively completed assembly of the mask of FIG. 8.

In an alternative situation in which an inflatable cushion is an added feature on the exposed backside of plate 50' and the adjacent inflatable ring (71) surface, in accordance with teachings of my copending U.S. application Ser. No. 952,586, filed Sep. 28, 1992, the inflatable cushion need merely cover the unsealed location of "cut-out" 76 around tubular formation 70, whereby to enable inflation of ring 71 to concurrently inflate the cushion, and deflation of ring 71 to concurrently deflate the cushion; however, for more reliable concurrent inflation of ring 71 and the cushion, it is preferred to drill an aperture 78 in the skirt of FIG. 9 near but offset above flange 37, for assured air communication between ring 71 and the cushion. As explained in said application Ser. No. 952,586, the inflated condition of the cushion, which may have a potentially inflated contour suggested by phantom line 77, enables the cushion to bear against the back wall of the pharynx for gently loaded application of inflatable ring 71 into its intended sealing engagement with the laryngeal inlet. More specifically, the cushion schematically indicated in FIG. 8 comprises a suitably cut shell of thin flexible material adhered peripherally to the equator (suggested at 79) of the inflatable ring 71 and suitably apertured to fit around and be adhesively sealed to the two tubular members 50' and 72.

The described embodiments of the invention will be seen to meet stated objects, significantly reducing the complexity and cost to manufacture each of a variety of laryngeal-mask configurations. In addition to the advantage of being able to produce the inflatable ring with uniformly controlled material thickness, there is a further advantage which may not be immediately apparent; this further advantage results from cooperating factors which follow from (a) producing the inflatable ring with uniform or precision-controlled thickness, and (b) inverting the pre-moulded skirt to create the ring in a naturally toroidal envelope wherein inner and outer circumferential surfaces of the envelope are in lightly but uniformly stressed opposition, so that circumferential compressional stress at the inner surface of the envelope is in equilibrium with circumferential hoop-tension stress at the outer surface of the envelope. The fact that wall thickness is circumferentially uniform accounts for natural circumferential uniformity in the ring section. The fact that this uniform thickness can be reliably made thinner than the "nominal" greater thickness of prior constructions is responsible (a) for greater flexible collapse of the mask to a smaller, more pliable structure when evacuated (for insertion in or removal from a patient), and (b) for more compliantly adapted conformability with abutting profile features of the laryngeal inlet when inflated in installed position.

More specifically with respect to the indicated equilibrium between opposed compressional and hoop-tension stresses, it will be understood that, upon completion of any of the intermediate products of FIGS. 2, 4B, 6 and 9, the involved thin flexible skirts are in relatively unstressed condition while still in the shape to which they were moulded. Inverting the skirt brings the lower edge of the skirt into adjacency (if not into circumferentially continuous engagement) with the moulded upper edge of the skirt, so that what was the outer surface of the skirt is thereafter the inner surface of the inflatable ring; at the same time, what had been the inner surface of the skirt is thereafter the outer surface of the inflatable ring. However thin the moulded thickness of the skirt, it necessarily follows that the moulded inner surface of the skirt is of less circumferential extent than the circumferential extent of the moulded outer surface. But on skirt inversion, what was an inner surface of unstressed lesser circumferential extent becomes an outer surface of necessarily greater, but tension-stressed, circumferential extent; at the same time, on skirt inversion, what had been an outer surface of unstressed greater circumferential extent becomes an inner surface of necessarily lesser, but compression-stressed, circumferential extent. It is these two opposing stresses, attributable to forced opposing changes in peripheral extent, that account for the indicated equilibrium, regardless of moulded skirt thickness, even for presently preferred relatively thin skirt-thickness dimensions in the range 0.4 to 1.0 mm, it being noted that laryngeal masks must be made in a range of sizes, including a range of inflatable-ring thickness, for best accommodation to laryngeal-inlet dimensions of the patient, whatever his age and stage of physical development. Within the stated range of inflatable-ring thickness, it is presently preferred to mould the skirt to a thickness of substantially 0.7 mm, a dimension which is recommended for most laryngeal masks of adult-patient sizes.

What is claimed is:

1. A laryngeal-mask construction, comprising a backplate member providing an essentially a single plane an apertured base-mounting rim of generally elliptical configuration, and an inflatable toroidal ring of flexible material, the radially inner circumference of which is connected to the periphery of said rim, said ring having a generally toroidal wall having an inner toroidal wall surface and an outer toroidal wall surface, said ring having a port connection that is locally open through said inner and outer toroidal wall surfaces, and the inner toroidal wall surface when uninflated being compressionally stressed in opposition to tensional stress of the outer torroidal wall surface.

2. The construction of claim 1, in which the material of said back-plate member is the same as and an integrally formed unit with said ring.

3. The construction of claim 2, in which said material is relatively thick in the formation of said backplate member and is relatively thin in the formation of said ring.

4. The construction of claim 1, in which said backplate member and said inflatable ring are separate elements, in circumferentially sealed assembly at said rim.

5. A laryngeal-mask construction, comprising a backplate member providing in essentially a single plane an aperture base-mounting rim of generally elliptical configuration, and an inflatable toroidal ring of flexible material, the radially inner circumference of which is connected to the periphery of said rim, said ring having a generally toroidal wall with an inner surface and an outer surface, said ring having a port connection that is locally open through said inner and outer surfaces, and the inner surface of said wall being compressionally stressed in opposition to circumferential tension of the outer surface of said wall, the generally elliptical configuration of said rim having a major axis of symmetry extending from a more rounded proximal end to a more pointed distal end, and said back-plate member including a proximally directed formation above said plane and adapted for airway-tube connection on an axis directed to a point within said rim, the axis of said proximally directed formation being at an acute angle to said single plane and in a geometric plane that includes said major axis and is normal to said single plane.

6. The construction of claim 5, and including an airway tube connected to said proximally directed formation.

7. A laryngeal-mask construction, comprising a back-plate member providing in essentially a single plane an apertured base-mounting rim of generally elliptical configuration, and an inflateable toroidal ring of flexible material, the radially inner circumference of which is connected to the periphery of said rim, said ring having a generally toroidal wall with an inner surface and an outer surface, said ring having a port connection that is locally open through said inner and outer surfaces, and the inner surface of said wall being compressionally stressed in opposition to circumferential tension of the outer surface of said wall, said rim comprising upper and lower adhesively retained component parts of circumferentially lapped generally elliptical configuration, said rim configuration of both said parts having a major axis of symmetry extending from a more rounded proximal end to a more pointed distal end; said back-plate member integrally including the upper one of the parts of said rim and also including a proximally directed formation above said upper rim part, said proximally directed formation being adapted for airway-tube connection on an axis directed to a point within said rim, the axis of said proximally directed formation being at an acute angle to said single plane and in a geometric plane that includes said major axis and is normal to said single plane; and the lower one of the parts of said rim being an integral formation with said inflatable ring.

8. In a laryngeal mask construction wherein a back-plate member provides in essentially a single geometric plane an apertured base-mounting rim of generally elliptical configuration to define a lumen with an inflatable ring of flexible material the inner circumference of which is connected to the periphery of said rim, the improvement in which said inflatable ring is the product of inverting a pre-molded skirt of uniformly thin flexible material peripherally continuously connected at one end to said rim and extending from said rim in an axial direction generally normal to said plane, said skirt having an outwardly bulging body and terminating at a lower edge of substantially the peripheral extent of the connection to said rim, the extent in said axial direction being substantially equal to the circumferential extent of a section of said ring wherein the section is taken in a section plane (a) which includes said axial direction, and (b) wherein the section plane is in a single radial direction away from said axial direction, said skirt being inverted to the extent of flexibly defining said ring peripherally continuously around said rim, with the bulging body of the skirt externally surrounding said rim and the inverted lower edge of the skirt downwardly directed within the inverted bulging body and into peripherally sealed relation with said one-end connection to said rim.

9. The construction of claim 8, in which said pre-molded skirt integrally includes a distally projecting tubular formation which on skirt inversion is proximally directed into adjacency with at least a portion of said back-plate member and is adapted for flexible drainage-tube connection, and an inflatable back cushion comprising a shell of flexible material adhered generally to the perimeter of said inflatable ring to define said inflatable back cushion in conjunction with said mask construction, there being an air passage communicating between said inflatable ring and said inflatable cushion 10. The construction of claim 8, in which said pre-molded skirt integrally includes a distally projecting tubular formation which on skirt inversion is proximally directed into adjacency with at least a portion of said back-plate member and is adapted for flexible drainage-tube connection.

11. The construction of claim 8, and an inflatable cushion comprising a shell of flexible material adhered generally to the perimeter of said inflatable ring to define said inflatable back cushion in conjunction with said mask construction, there being an air passage communicating between said inflatable ring and said inflatable cushion.

12. The construction of claim 8, in which said pre-molded skirt integrally includes a tubular projection that is distally projecting inwardly of said skirt from a location on the outward bulge of said body, said tubular projection being proximally directed and projecting externally of said inflatable ring on skirt inversion.

13. The construction of claim 8, and including an airway tube connected at one end to said back-plate member for airway tube communication through said lumen.

* * * * *